(12) United States Patent
Grases Freixedas et al.

(10) Patent No.: US 11,213,535 B2
(45) Date of Patent: Jan. 4, 2022

(54) COMPOSITION CONTAINING PHYTIC ACID, MAGNESIUM AND POLYPHENOLS FOR THE TREATMENT OR PREVENTION OF RENAL LITHIASIS

(71) Applicant: UNIVERSITAT DE LES ILLES BALEARS, Palma de Mallorca (ES)

(72) Inventors: Félix Grases Freixedas, Palma de Mallorca (ES); Antonia Costa Bauzá, Palma de Mallorca (ES); Rafael María Prieto Almirall, Palma de Mallorca (ES); Adrián Rodríguez Rodríguez, Palma de Mallorca (ES)

(73) Assignee: UNIVERSITAT DE LES ILLES BALEARS, Palma de Mallorca (ES)

( * ) Notice: Subject to any disclaimer, the term of this patent is extended or adjusted under 35 U.S.C. 154(b) by 0 days.

(21) Appl. No.: 15/319,546

(22) PCT Filed: Apr. 14, 2015

(86) PCT No.: PCT/ES2015/070296
§ 371 (c)(1),
(2) Date: Dec. 16, 2016

(87) PCT Pub. No.: WO2015/197892
PCT Pub. Date: Dec. 30, 2015

(65) Prior Publication Data
US 2017/0128469 A1    May 11, 2017

(30) Foreign Application Priority Data
Jun. 25, 2014  (ES) .............................. ES201430961

(51) Int. Cl.
| | |
|---|---|
| *A61P 13/12* | (2006.01) |
| *A61K 33/06* | (2006.01) |
| *A61K 33/08* | (2006.01) |
| *A61K 31/6615* | (2006.01) |
| *A61P 13/04* | (2006.01) |
| *A61K 36/87* | (2006.01) |
| *A61K 31/353* | (2006.01) |
| *A61K 31/05* | (2006.01) |
| *A61K 33/10* | (2006.01) |
| *A61K 31/192* | (2006.01) |
| *A61K 31/7024* | (2006.01) |
| *A61K 45/06* | (2006.01) |
| *A23L 33/105* | (2016.01) |
| *A61K 36/48* | (2006.01) |
| *A61K 36/899* | (2006.01) |

(52) U.S. Cl.
CPC ........ *A61K 31/6615* (2013.01); *A23L 33/105* (2016.08); *A61K 31/05* (2013.01); *A61K 31/192* (2013.01); *A61K 31/353* (2013.01); *A61K 31/7024* (2013.01); *A61K 33/06* (2013.01); *A61K 33/08* (2013.01); *A61K 33/10* (2013.01); *A61K 36/48* (2013.01); *A61K 36/87* (2013.01); *A61K 36/899* (2013.01); *A61K 45/06* (2013.01); *A61P 13/04* (2018.01)

(58) Field of Classification Search
CPC ..... A61P 13/12; A61K 31/6615; A61K 31/06; A61K 31/08
See application file for complete search history.

(56) References Cited

U.S. PATENT DOCUMENTS 5,219,889 A * 6/1993 Walsdorf .............. A61K 31/19
514/574

FOREIGN PATENT DOCUMENTS

| | | | |
|---|---|---|---|
| ES | 2 058 025 | A1 | 10/1994 |
| ES | 2058025 | A1 * | 10/1994 |
| FR | 2 826 361 | A1 | 12/2002 |
| JP | 2012 188685 | A | 10/2012 |

OTHER PUBLICATIONS

F Grases, A Costa-Bauza, RM Prieto, A Conte, A Servera, Renal papillary calcification and the development of calcium oxalate monohydrate papillary renal calculi: a case series study; BMC Urol, 2013, 13: 14, pp. 1-7.
F Grases, RM Prieto, p. Sanchis, C Saus, T De Francisco, Role of phytate and osteopontin in the mechanism of soft tissue calcification; J Nephrol, 2008, 21(5), pp. 768-775.
Wu N et al: "Effects of magnesiumcitrate and phytin on reducing urinary calcium excretion in rats", World Journal of Urology, Springer International, DE, vol. 12, No. 6, Dec. 1, 1994 (Dec. 1, 1994) pp. 323-328.
Grases Felix et al: "Phytate acts as an inhibitor in formation of renalcalculi", Frontiers in Bioscience, Frontiers in Bioscience, Albertson, NY, US, vol. 12, Jan. 1, 2007 (Jan. 1, 2007), pp. 2580-2587.
Felix Grases et al: "Phytotherapy and renal stones: the role of antioxidants. A pilot study in Wistar rats", Urological Research ; A Journal of Clinical and Laboratory Investigation in Urolithiasis and Related Areas, Springer, Berlin, DE, vol. 3 7, No. 1, Dec. 10, 2008 (Dec. 10, 2008), pp. 35-40.
Amengual-Cladera Emilia et al: "Phytotherapy in a rat model of hyperoxaluria: the antioxidant effects of quercetin involve serum paraoxonase 1 activation", Experimental Biology and Medicine, Society for Experimental Biology and Medicine, US, vol. 236, No. 10, Oct. 1, 2011 (Oct. 1, 2011), pp. 1133-1138.
Johansson G et al: "Effects of magnesiumhydroxide in renalstone disease", Journal of the American College of Nutrition, American College of Nutrion, Wilmington, NC, US, vol. 1, No. 2, Jan. 1, 1982(Jan. 1, 1982) pp. 179-185.

(Continued)

Primary Examiner — Gina C Justice
(74) Attorney, Agent, or Firm — Leason Ellis LLP

(57) ABSTRACT

The present invention is related to a composition comprising phytic acid or a phytate salt, magnesium in the form of salt, hydroxide or oxide and optionally at least one polyphenol. These components may be in isolated form or be part of an enriched plant extract. The invention is also related to the use of this composition for the treatment of renal lithiasis, preferably calcium or calcium oxalate lithiasis, either in the form of a medicament, a nutraceutical or functional food or food supplement.

19 Claims, 1 Drawing Sheet

(56) References Cited

OTHER PUBLICATIONS

Vitali D et al: "Bioaccessibility of Ca, Mg, Mn and Cu from whole grain tea-biscuits: Impact of proteins, phytic acid and polyphenols", Food Chemistry, Elsevier Ltd, NL, vol. 110, No. I, Sep. 1, 2008 (Sep. 1, 2008), pp. 62-68.

R M Forbes et al: "Effects of dietary phytate, calcium and magnesium levels on zinc bioavailability to rats", The Journal of nutrition, Aug. 1, 1984 (Aug. 1, 1984), p. 1421.

Database WPI Week 201373 Thomson Scientific, London, GB; AN 2013-L99911, XP082741091, BR PI1 083 695 A2, Feb. 19, 2013, Pereira De Jesus H.

Database WPI , Week 201074, Thomson Scientific, London, GB; AN 2010-L41320, XP002741092, CN 101 885 236 A, Aug. 18, 1994, Cai R.

International Search Report and written opinion in corresponding PCT Application No. PCT/ES2015/070296, dated Jun. 29, 2015.

F. Grases, O. Sohnel, A. Costa-Bauza, Renal Stone Formation and development, International Urology and Nephrology, 31(5) pp. 591-600. (1999).

* cited by examiner

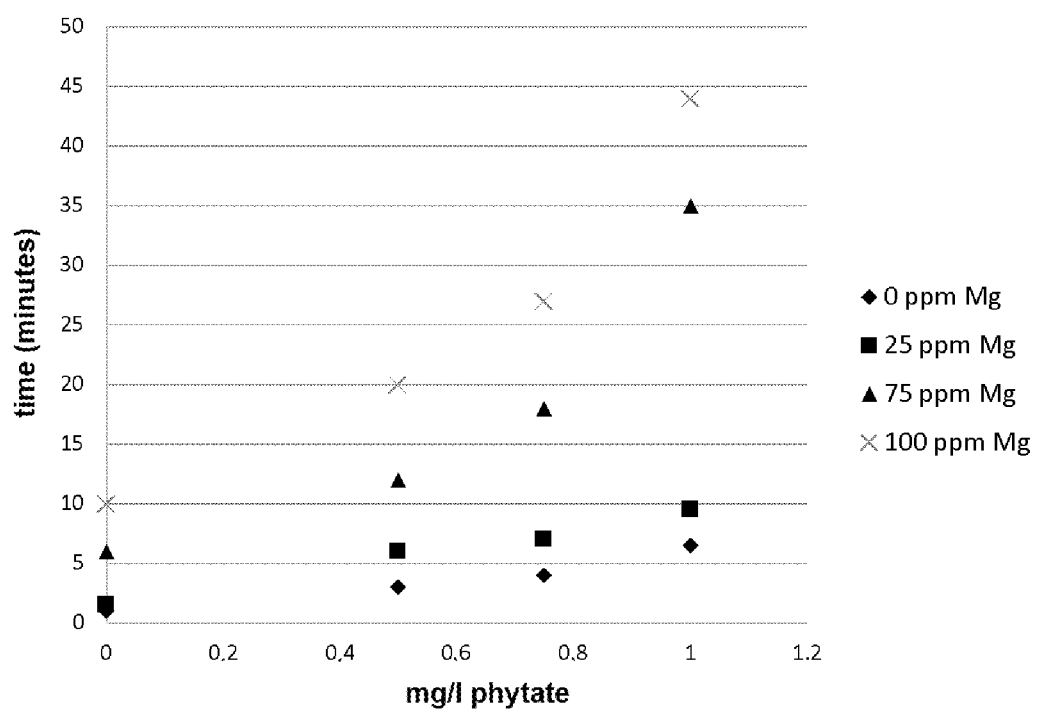

COMPOSITION CONTAINING PHYTIC ACID, MAGNESIUM AND POLYPHENOLS FOR THE TREATMENT OR PREVENTION OF RENAL LITHIASIS

CROSS-REFERENCE TO RELATED PATENT APPLICATIONS

This application is a U.S. National Phase Application under 35 U.S.C. § 371 of International Patent Application No. PCT/ES2015/070296, filed Apr. 14, 2015, and claims the priority of Spanish Application No. P201430961, filed Jun. 25, 2014. The International Application was published on Dec. 30, 2015 as International Publication No. WO 2015/197892 A1.

The present invention is related to a composition comprising phytic acid or any of its phytate, magnesium salts and optionally polyphenols, which is useful for the treatment of renal lithiasis, mainly of calcium renal lithiasis, due to the synergy between its components to inhibit the crystallization of calcium salts, the reduction of free oxalate and papillary injuries due to oxidative stress.

Thus, the present invention belongs to the field of pharmacology.

STATE OF THE ART

It is known that the ionic species of phytic acid (phytate) have the ability to inhibit the development of calcium salts deposits in biological fluids, thus reducing the risk of both calcium kidney stones and other pathological calcifications. It is also known that phytate, found in the tissues and fluids of mammals, comes mainly from the diet. Recently, it has been shown that the calcium oxalate monohydrate papillary kidney stones occur as a result of injuries originating from the tissue of the renal papilla (F Grases, A Costa-Bauza, R M Prieto, A Conte, A Servera, BMC Urol, 2013, 13: 14, doi: 10.1186/1471-2490-13-14). These injuries result in processes of tissue calcification in the form of hydroxyapatite in the intrapapillary tissue, which when increase in size and cross the epithelium covering the papilla and come into contact with the urine (which is permanently supersaturated in calcium oxalate) lead to the beginning of the development of the papillary calculi. The crystallization inhibitors together with the immune system can reverse this process since when the crystallization process is stopped the macrophages can destroy the incipiently formed hydroxyapatite (F Grases, R M Prieto, P Sanchis, C Saus, T De Francisco, J Nephrol, 2008, 21(5), 768-75). Obviously, the smaller the number of injuries, the smaller the probability of initiating the development process of the papillary calculi will be. Recent studies have shown that certain compounds with antioxidant properties, such as polyphenols, significantly reduce the development of intrapapillary calcifications (F. Grases, R M Prieto, I Gomila, P Sanchis, A Costa-Bauza, Urol Res, 2009, 37(1), 35-40), which is why they may have an important role in the prevention of renal lithiasis.

Calcium oxalate stones represent approximately 70% of the kidney stones, the level of urinary oxalate being an important risk factor for their development. The monitoring of free oxalate in urine is a very important aspect in the treatment against the development of calcium oxalate stones. Thus, magnesium, by forming soluble complexes with oxalate ion, significantly decreases calcium oxalate supersaturation, which results in increased difficulty to generate calcium oxalate crystals.

DESCRIPTION OF THE INVENTION

The object of the present invention is to present new formulas for the treatment of renal lithiasis, preferably calcium renal lithiasis, related with the aspects described in the section state of the art and with recent discoveries about the combination of phytic acid and/or its pharmaceutically acceptable phytates with polyphenols and magnesium salts. This combination can be very beneficial for the treatment of kidney stones, preferably calcium kidney stones, and more preferably calcium oxalate kidney stones, since the inhibitory capacity of the crystallization of calcium salts by phytate is added to the beneficial effect of polyphenols on the papillary injuries originated from oxidative stress. These two effects are combined with the capacity of magnesium to reduce the concentrations of free oxalate in urine, by forming soluble complexes with it and thus reducing the supersaturation with respect to calcium oxalate. Additionally, magnesium synergistically enhances the ability of phytate to inhibit the crystallization of calcium oxalate. The present invention provides a method for the treatment and prevention of renal calcifications by means of the combined use of phytate, polyphenols and/or magnesium salts, hydroxides or oxides.

Thus, a first aspect of the present invention is referred to a composition comprising phytic acid or any of its salts, which may be in an isolated form or in the form of an enriched plant extract, and magnesium in the form of salt, hydroxide or oxide.

The term 'calcifications' or 'stones' includes all such process or conditions which imply/induce the formation of solid precipitates in the urine. Thus, the conditions that induce calcifications or kidney stones include, but are not limited to, a high level of urinary oxalate, a high level in the urinary excretion of calcium or a reduced presence or activity of nucleation and crystal growth inhibitors.

The term 'urinary oxalate' is referred to the oxalate excretion in the urine. Between 8-30 mg/day are considered normal levels, while if they exceed 45 mg/day it is considered a situation of hyperoxaluria. The levels of oxalate in the urine can reach levels between 90 and 270 mg/day in patients with primary hyperoxaluria.

'Hypercalciuria' is referred to an elevated urinary calcium excretion which exceeds 300 mg/day or 4 mg/kg/day.

The 'reduced presence or activity of nucleation and crystal solids growth inhibitors' is referred to all those compounds that can modulate said process, which include but are not limited to glycoproteins such as nephrocalcin or osteopontin and certain inorganic and organic polyphosphates. These compounds interact with the crystals and inhibit their growth.

In the present invention, 'phytic acid' or 'myo-inositolhexaphosphate', is understood as the molecule of the formula:

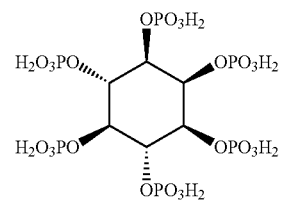

and 'phytate' is the form of phytic acid with at least one less hydrogen, so that the corresponding phosphate group interacts with a cation (K, Mg, Ca, Mn, Zn and Fe). The phytate salts of interest in the invention are mainly sodium, potassium, calcium, magnesium, zinc and calcium-magnesium salts.

In a preferred embodiment, the composition of the invention comprises at least one polyphenol.

In the present invention polyphenols means a group of chemicals found in plants characterized by the presence of more than one phenol group per molecule. These products have significant antioxidant properties and are also suitable for human consumption. The polyphenols with special interest for the composition of the invention are those extracted from the seeds of red grapes or white grapes, although they may come from other plant species such as berries, tea, beer, olive oil, chocolate/cocoa, nuts, pomegranates, etc. Specific examples of preferred polyphenols of the invention are epicatechin, catechin, gallocatechin, epigallocatechin, quercetin, resveratrol, tannic acid or gallic acid.

Thus, it has been shown in an 'in vivo' model using experimental animals that with a composition comprising 1% phytate with a supplement of polyphenols extracted from white grape seed, a reduction of 50% of renal calcification is achieved, such and as explained in example 2.

Other studies have shown that the presence of magnesium in artificial urine synergistically enhances the capacity of phytate to inhibit the crystallization of calcium oxalate, such and as shown in example 1.

Magnesium forms salts with phytate which are more soluble than calcium salts, therefore it increases the absorption of phytate in the intestine, resulting in an increase of the phytate excreted in the urine and thus an increase in its inhibitory capacity against the formation of calcium oxalate kidney stones.

These models show that a formulation comprising phytate in a form additionally containing polyphenols and/or magnesium salts or oxide, can be used for the manufacture of medicaments or dietary supplements for the treatment or prophylaxis of renal lithiasis, preferably calcium renal lithiasis, and more preferably oxalocalcium renal lithiasis.

For the purposes of the present invention, phytic acid and/or its pharmaceutically acceptable salts may be used in free form as pure substances, extracts of plant species containing them, such as, for example, extracts of white or brown rice, or carried by plant species containing them, such as the germs or the external parts of the wheat, oat, soy, almond, locust bean, etc. grains or fruits.

Polyphenols may also be used in free form as pure substances or as extracts of plant species containing them or that are pharmaceutically acceptable.

Magnesium may be supplied in the form of its pharmaceutically acceptable salts such as for example magnesium oxide, magnesium hydroxide, magnesium citrate, magnesium stearate, magnesium carbonate, magnesium chloride and magnesium sulfate.

In a preferred embodiment, the composition of the invention comprises between 40 and 50% by weight of phytic acid or its salts.

In a preferred embodiment, the composition of the invention comprises between 25 and 40% by weight of magnesium in the form of salt, hydroxide or oxide.

In a preferred embodiment, the composition of the invention comprises between 10-30% by weight of polyphenols.

Another aspect of the invention is related to the use of the composition of the invention for the manufacture of a medicament.

Another aspect of the invention is related to the use of the composition described for the manufacture of a medicament for the treatment of renal lithiasis. Preferably, renal lithiasis is calcium renal lithiasis.

Another aspect of the invention is related to the use of the composition of the invention for the preparation of a medicament intended to reduce the risks and improve the health status of patients with diseases related with the crystallization of calcium oxalate.

A very important advantage of using the combination of phytate, polyphenols and magnesium is that the action of an inhibitor of the calcium oxalate crystallization is combined with the action of the polyphenols which, by avoiding or reducing the injuries of the papillary tissue, also reduce the number of heterogeneous nucleators of calcium oxalate, and with the action of magnesium, that forms soluble complexes with oxalate, thus decreasing urinary supersaturation of calcium oxalate.

The combination of phytate, polyphenols and magnesium may be administrated in solid form (including granules, powders or suppositories) or in liquid form (such as solutions, suspensions or emulsions). In turn, they may be administered as such or after being subjected to operations such as sterilization, addition of preservatives, addition of stabilizers or addition of emulsifiers.

The coadministration of phytate, polyphenols and magnesium may be combined with one or more compounds which facilitate absorption thereof through the route of administration selected. Thus, they can be administered with lactose, sucrose, talc, magnesium stearate, cellulose, calcium salts, gelatin, fatty acids, as well as with other pharmaceutically acceptable substances.

The pharmaceutical compositions containing phytate, polyphenols and magnesium include an amount of each active principle that allows effectively reducing the urinary oxalate levels. The effective amounts for this purpose depend on factors such as the route of administration, the health of the individual or the oxalate urinary levels, although these factors do not limit the inclusion of others that help define the recommended amounts. In any case, it is understood that the amounts of each active principle that each individual will take will be determined by a specialist depending on individual circumstances. In a preferred embodiment, the composition is in a suitable dosage for administration of between 500 mg/day and 1,000 mg/day.

The term 'renal lithiasis', 'urolithiasis' or 'nephrolithiasis' is referred to the disorder caused by the presence of calculi or stones inside the kidneys or the urinary tract (ureters, bladder). Kidney stones are composed of substances that are normal in urine (calcium salts, uric acid, cystine etc.) which for different reasons have concentrated and precipitated forming fragments of larger or smaller size.

The term 'uric acid crystals' or 'uric acid stones' includes all such process or conditions which imply/induce the formation of solid precipitates in the urine wherein this substance is involved.

In a preferred embodiment, the composition is a pharmaceutical composition or a nutraceutical or functional food.

In the present invention 'nutraceutical' or 'functional food' is understood as a food that has a beneficial effect on health. In the same way, the term nutraceutical can be applied to extracts or chemical compounds derived from common foods. Examples of foods that are attributed the nutraceutical properties are olive oil, red wine, broccoli, soy, etc. Nutraceuticals are normally used in nutritional mixtures and in the pharmaceutical industry. In the same way as some foods may be classified as nutraceuticals, some nutritional supplements are also classified as such, as, for example, fatty acids such as omega-3 derived from fish oil and some vegetables or antioxidants and vitamins.

The pharmaceutically acceptable adjuvants and vehicles that may be used in said compositions are the adjuvants and vehicles known by the persons skilled in the art and commonly used in the preparation of therapeutic compositions.

Throughout the description and the claims the word 'comprises' and its variants are not intended to exclude other technical features, additives, components or steps. For those skilled in the art, other objects, advantages and features of the invention will become apparent in part from the description and in part from the practice of the invention. The following examples and FIGURE are provided by way of illustration, and are not intended to be limiting of the present invention.

BRIEF DESCRIPTION OF THE FIGURES

FIG. 1. It shows the graphical representation of the induction times of the crystallization (in minutes) for a 200 mg/L calcium and 50 mg/L oxalate solution, in synthetic urine, at different magnesium and phytate concentrations.

EXAMPLES

Example 1. Measurement of the Crystallization of Calcium Oxalate in the Presence of Magnesium and Phytate From a 200 mg/L calcium and 50 mg/L oxalate solution, in synthetic urine, the induction times for the crystallization of calcium oxalate have been calculated in the presence of different phytate and/or magnesium concentrations. Table 1 shows said induction times, which as it can be clearly seen in FIG. 1, increase with the increase in the concentration of magnesium and phytate. Thus, when there is neither magnesium nor phytate, the calcium oxalate takes 1 minute to crystallize. This time increases up to 10 minutes when 100 mg/L magnesium is added and, in turn, it increases up to 44 minutes if, in addition to the 10 mg/L magnesium, 1 mg/L phytate is added.

TABLE 1 induction times of crystallization (in minutes) for a 200 mg/L calcium and 50 mg/L oxalate solution, in synthetic urine, at different concentrations of magnesium and phytate.

| mg/L phytate | 0 mg/L Mg t (min) | 25 mg/L Mg t (min) | 75 mg/L Mg t (min) | 100 mg/L Mg t (min) |
|---|---|---|---|---|
| 0 | 1 | 1.5 | 6 | 10 |
| 0.5 | 3 | 6 | 12 | 20 |
| 0.75 | 4 | 7 | 18 | 27 |
| 1 | 6.5 | 9.5 | 35 | 44 |

Example 2. Effect of the Composition of the Invention on Wistar Rats Subjected to a Lithogenic Diet A group of Wistar rats was pre-treated with polyphenols extracted from white grape seeds (added to the drinking water in concentrations of 200 mg/L) and phytate (1% of the solid diet fed to the animals, in the form of phytin, which is the calcium magnesium salt). Subsequently, papillary renal lithiasis was induced by administration of ethylene glycol and the preventive treatment was continued. The antilithiatic activity of the polyphenol+phytate mixture was evaluated through the calcium content of the kidneys of the animals (extracted at the end of the experiment) and the corresponding histological studies of the renal tissue, by comparison with the corresponding control groups. It was observed that the applied prophylactic treatment reduced renal calcification by 50%.

Example 3. Effect of the Composition of the Invention on Patients with Problems of Renal Lithiasis In this example three pharmaceutical compositions of the present invention are illustrated.

Composition 1.

| Compound | Amount |
|---|---|
| Calcium-magnesium phytate | 300 mg |
| Magnesium citrate | 250 mg |
| Epicatechin | 100 mg |

Composition 2.

| Compound | Amount |
|---|---|
| Calcium-magnesium phytate | 300 mg |
| Magnesium citrate | 250 mg |
| Catechin | 150 mg |

Composition 3.

| Compound | Amount |
|---|---|
| Brown rice extract equivalent to an amount of phytate of | 250 mg |
| Magnesium oxide | 150 mg |
| Black grape seed extract equivalent to an amount of polyphenols of | 150 mg |

Composition 4.

| Compound | Amount |
|---|---|
| Locust bean germ extract and dry wheat extract equivalent to an amount of phytate of | 150 mg |
| Magnesium oxide | 100 mg |
| White grape seed extract equivalent to an amount of polyphenols of | 90 mg |

200 mg of calcium-magnesium phytate (phytin) together with 200 mg of magnesium citrate and 100 mg of quercetin were orally administered to a patient, twice a day, at breakfast and after dinner. After the treatment, it was observed that the inhibitory capacity of the urine of the patient against the crystallization of calcium oxalate increased 40% with respect to the urine of the own patient before ingesting phytate. The antioxidant capacity of the urine (potentiometrically evaluated using a platinum electrode) increased 15%. These variations may imply from a significant reduction of the recurrence to a total elimination of the calculogenesis process because they eliminate and/or normalize key factors in the calculogenesis process, such as the inhibitory capacity of the urine, oxaluria and the protection against oxidative stress.

The invention claimed is:

1. A method for treating a patient with renal lithiasis, comprising:
administering to the patient a composition comprising phytic acid or a salt thereof, magnesium oxide, and magnesium stearate,
wherein the composition comprises between 25% and 40% by weight of the magnesium compounds; and wherein the renal lithiasis is oxalocalcium renal lithiasis, and wherein the oxalocalcium renal lithiasis is related to the crystallization of calcium oxalate, and wherein the composition synergistically inhibits crystallization of calcium oxalate.

2. The method of claim 1, wherein administration of the composition reduces the risks and improve the health status of the patient in relation to the crystallization of calcium oxalate.

3. The method of claim 1, wherein the composition is in a suitable dosage for administration of between 500 mg/day and 1,000 mg/day.

4. The method of claim 1, wherein the composition further comprises at least one polyphenol.

5. The method of claim 4, wherein the at least one polyphenol is selected from the group consisting of: epicatechin, catechin, gallocatechin, epigallocatechin, quercetin, resveratrol, gallic acid and tannic acid.

6. The method of claim 4, wherein the at least one polyphenol is in the form of plant extract from grape seed.

7. The method of claim 1, wherein the composition comprises between 40% and 50% by weight of phytic acid or its salt.

8. The method of claim 4, wherein the composition comprises between 10% and 30% by weight of polyphenols.

9. The method of claim 1, wherein the composition further comprises lactose, sucrose, talc, cellulose, calcium salts, gelatin or fatty acids.

10. The method of claim 1, wherein the composition is in the form of a pharmaceutical composition, functional food, a nutraceutical product, or a food supplement.

11. A method for treating a patient with renal lithiasis, comprising:
administering to the patient a composition comprising (i) phytic acid or a salt thereof, and (ii) a magnesium compound selected from the group consisting of: magnesium oxide, magnesium hydroxide, magnesium citrate, magnesium stearate, magnesium carbonate, magnesium chloride, magnesium sulfate, and a combination thereof;
wherein the composition comprises between 25% and 40% by weight of the magnesium compound; and wherein the renal lithiasis is oxalocalcium renal lithiasis, which is related to the crystallization of calcium oxalate, and wherein the composition synergistically inhibits crystallization of calcium oxalate.

12. The method of claim 11, wherein the composition is in a suitable dosage for administration of between 500 mg/day and 1,000 mg/day.

13. The method of claim 11, wherein the composition further comprises at least one polyphenol.

14. The method of claim 13, wherein the at least one polyphenol is selected from the group consisting of: epicatechin, catechin, gallocatechin, epigallocatechin, quercetin, resveratrol, gallic acid and tannic acid.

15. The method of claim 13, wherein the at least one polyphenol is in the form of plant extract from grape seed.

16. The method of claim 13, wherein the composition comprises between 10% and 30% by weight of polyphenols.

17. The method of claim 11, wherein the composition comprises between 40% and 50% by weight of phytic acid or its salt.

18. The method of claim 11, wherein the composition further comprises lactose, sucrose, talc, cellulose, calcium salts, gelatin or fatty acids.

19. The method of claim 11, wherein the composition is in the form of a pharmaceutical composition, functional food, a nutraceutical product, or a food supplement.

* * * * *